US012594055B1

(12) United States Patent
Murray

(10) Patent No.: US 12,594,055 B1
(45) Date of Patent: Apr. 7, 2026

(54) PROBE-SECURING APPARATUS

(71) Applicant: Big Ridge Solutions, LLC, Post Falls, ID (US)

(72) Inventor: Johnathan Murray, Post Falls, ID (US)

(73) Assignee: Big Ridge Solutions, LLC, Post Falls, ID (US)

( * ) Notice: Subject to any disclaimer, the term of this patent is extended or adjusted under 35 U.S.C. 154(b) by 489 days.

(21) Appl. No.: 18/130,318

(22) Filed: Apr. 3, 2023

Related U.S. Application Data

(60) Provisional application No. 63/327,029, filed on Apr. 4, 2022.

(51) Int. Cl.
| | |
|---|---|
| *G01N 29/22* | (2006.01) |
| *A61B 8/00* | (2006.01) |
| *G01N 29/265* | (2006.01) |
| *G01N 29/28* | (2006.01) |

(52) U.S. Cl.
CPC .......... *A61B 8/4477* (2013.01); *A61B 8/4218* (2013.01); *G01N 29/225* (2013.01); *G01N 29/265* (2013.01); *G01N 29/28* (2013.01)

(58) Field of Classification Search
CPC .. A61B 8/4477; A61B 8/4218; G01N 29/225; G01N 29/265; G01N 29/28
See application file for complete search history.

(56) References Cited

U.S. PATENT DOCUMENTS

| | | | | |
|---|---|---|---|---|
| 3,612,987 A | * | 10/1971 | Placke | G01N 27/9013 |
| | | | | 324/242 |
| 5,007,291 A | * | 4/1991 | Walters | G01N 29/223 |
| | | | | 226/176 |
| 2015/0329221 A1 | * | 11/2015 | Georgeson | H04L 41/0695 |
| | | | | 702/36 |
| 2022/0412921 A1 | * | 12/2022 | Jack | G01N 29/225 |

* cited by examiner

*Primary Examiner* — Xin Y Zhong
(74) *Attorney, Agent, or Firm* — Iron Summit IP

(57) ABSTRACT

Techniques associated with an apparatus that is configured to support probes during data collection. An example apparatus may include a base. The example apparatus may also include a mechanism coupled to the base. The mechanism may include means for detachably coupling a probe to the mechanism. In some examples, the mechanism may be configured to apply an amount of force associated with obtaining a measurement from the probe. In some examples, the apparatus may include multiple mechanisms for supporting multiple probes during data collection. These multiple probes may be able to generate data associated with different portions of a material being scanned.

20 Claims, 10 Drawing Sheets

PROBE ADAPTER
(E.G., BRACKET STYLE)
202(1)

MECHANISM
104(1)

PROBE
106(1)

APPARATUS
100

PROBE ADAPTER
(E.G., CLAMP STYLE)
202(2)

PROBE
106(2)

PROBE
106(3)

MECHANISM
104(2)

PROBE ADAPTER
(E.G., BRACKET STYLE)
202(3)

MECHANISM
104(3)

BASE
102

X

Y

Z

MECHANISM
104(3)

PROBE ADAPTER
(E.G., BRACKET STYLE)
202(3)

ROD END
702

GUIDE
(E.G., CARRIAGE)
510

GUIDE
(E.G., RAIL)
508

BASE
102

1000

PROBE-SECURING APPARATUS

CROSS-REFERENCE TO RELATED APPLICATION

This application claims priority to U.S. Provisional Application No. 63/327,029, filed Apr. 4, 2022, which is incorporated herein by reference in its entirety and for all purposes.

TECHNICAL FIELD

The present disclosure relates generally to an apparatus that, among other things, can be used to secure and/or position one or more probe(s) during an inspection, such as an ultrasonic inspection.

BACKGROUND

Ultrasonic testing is a technique that utilizes high frequency sound waves to locate cracks or other hidden flaws in structural materials (e.g., metals, composites, lumber, plastics). As such, ultrasonic testing can be used to determine the integrity of structural materials used in the construction of many industrial applications, such as bridges, buildings, dams, mines, energy production plants, or the like. In some scenarios, such as in the case of a hollow structural material (also referred to in industry as an "HSM"), there is no reasonable or nondestructive way to inspect the inside structure of the HSM in the absence of ultrasonic inspection techniques.

In some cases, hollow structural materials can be used as brace frames in structures where, if the brace frame fails, the entire structure is compromised. Additionally, the integrity of a hollow structural material can deteriorate over time due to environmental factors (e.g., moisture causing rusting of metals), stress, use, or the like. As such, performing routine inspections on hollow structural materials to check for deterioration can be extremely important. However, in some situations, performing ultrasonic scanning on these structures can be impractical.

SUMMARY

One general aspect of this disclosure relates to an apparatus. The apparatus may include a base. The apparatus may also include a first mechanism coupled to the base, the first mechanism may include first means for detachably coupling a first probe to the first mechanism, the first mechanism may also be configured to apply an amount of force associated with obtaining a first measurement from the first probe. The apparatus may also include a second mechanism coupled to the base, the second mechanism may include second means for detachably coupling a second probe to the second mechanism, the second mechanism may be configured to apply the amount of force associated with obtaining a second measurement from the second probe.

Implementations may include one or more of the following features. The apparatus where: the base includes a cavity, the first mechanism is coupled to the base proximate a first side of the cavity, and the second mechanism is coupled to the base proximate a second side of the cavity. In some examples, the first side is opposite the second side, the first mechanism is further configured to extend the first means in a first direction that is substantially parallel to a plane defined by the base and into an area defined by the cavity, and the second mechanism is further configured to extend the second means in a second direction that is opposite the first direction, substantially parallel to the plane defined by the base, and into the area defined by the cavity. The base further includes a first flange and a second flange, the first flange extending proximate the first mechanism and the second flange extending proximate the second mechanism. The first mechanism and the second mechanism may include at least one of: pneumatic cylinders, hydraulic cylinders, gas springs, or mechanical springs. The apparatus may include a third mechanism coupled to the base, the third mechanism may include third means for detachably coupling a third probe to the third mechanism, the third mechanism configured to apply the amount of force or a different amount of force associated with obtaining a third measurement from the third probe. In some examples, the base includes a cavity, the first mechanism is coupled to the base proximate a first side of the cavity, the second mechanism is coupled to the base proximate a second side of the cavity opposite the first side, and the third mechanism is coupled to the base proximate a third side of the cavity between the first side and the second side. In some examples, the first mechanism is further configured to extend the first means in a first direction that is substantially parallel to a plane defined by the base and into an area defined by the cavity, the second mechanism is further configured to extend the second means in a second direction that is opposite the first direction, substantially parallel to the plane defined by the base, and into the area defined by the cavity, and the third mechanism is further configured to extend the third means in a third direction that is substantially perpendicular to the first direction and the second direction, substantially parallel to the plane defined by the base, and into the area defined by the cavity. The apparatus may include third means for retaining a fluid applicator. In some examples, the first means may include a first bracket for detachably coupling the first probe to the first mechanism, the first bracket configured to detachably couple to a first end of a first rod associated with the first mechanism, and the second means may include a second bracket for detachably coupling the second probe to the second mechanism, the second bracket configured to detachably couple to a second end of a second rod associated with the second mechanism.

One general aspect includes an apparatus for supporting multiple probes during performance of an ultrasonic test (e.g., a phased array ultrasonic test). The apparatus also includes a base plate including a cavity. The apparatus also includes a first pneumatic cylinder disposed proximate a first side of the cavity and substantially parallel to a plane defined by the base plate, the first pneumatic cylinder may include: a first body coupled to the base plate proximate the first side of the cavity, a first rod that extends in a first direction into an area defined by the cavity, and first means for detachably coupling a probe to the first rod. The apparatus also includes a second pneumatic cylinder disposed proximate a second side of the cavity opposite the first side of the cavity and substantially parallel to the plane defined by the base plate, the second pneumatic cylinder may include: a second body coupled to the base plate proximate the second side of the cavity, a second rod that extends in a second direction opposite the first direction and into the area defined by the cavity, and second means for detachably coupling the probe to the second rod.

Implementations may include one or more of the following features. The apparatus may include a third pneumatic cylinder disposed proximate a third side of the cavity between the first side and the second side and substantially parallel to the plane defined by the base plate, the third pneumatic cylinder may include: a third body coupled to the base plate proximate the third side of the cavity, a third rod that extends in a third direction that is substantially perpendicular to the first direction and the second direction and into the area defined by the cavity, and third means for detachably coupling the probe to a third end of the third rod. The apparatus may include third means for retaining a fluid applicator. The base plate further includes a first flange and a second flange, the first flange extending proximate the first pneumatic cylinder and the second flange extending proximate the second pneumatic cylinder. In some examples, the first means may include a first bracket for detachably coupling the probe to the first rod, the first bracket configured to detachably couple to the first rod, and the second means may include a second bracket for detachably coupling the probe to the second rod, the second bracket configured to detachably couple to the second rod.

One general aspect includes a method associated with performing an ultrasonic test of a structural material. The method also includes positioning the structural material within a cavity associated with an apparatus, the apparatus configured to secure probes during a data collection phase of the ultrasonic test. The method also includes configuring a first mechanism of the apparatus that is coupled to a first probe to apply an amount of force to the first probe, the amount of force associated with obtaining a first measurement from the first probe. The method also includes configuring a second mechanism of the apparatus that is coupled to a second probe to apply the amount of force to the second probe, the amount of force associated with obtaining a second measurement from the second probe. The method also includes causing a movement of the apparatus along a portion of the structural material in association with generating ultrasonic data during the data collection phase of the ultrasonic test.

Implementations may include one or more of the following features. The method where the first mechanism is a first pneumatic cylinder and configuring the first mechanism to apply the amount of force may include pressurizing the first pneumatic cylinder such that a pressure within the first pneumatic cylinder meets or exceeds a threshold pressure. The first probe captures first ultrasonic data associated with a first side of the structural material and the second probe captures second ultrasonic data associated with a second side of the structural material opposite the first side. The first mechanism and the second mechanism may include at least one of: pneumatic cylinders, hydraulic cylinders, gas springs, or mechanical springs. The method may include configuring a third mechanism of the apparatus that is coupled to a third probe to apply the amount of force or a different amount of force to the third probe.

BRIEF DESCRIPTION OF THE DRAWINGS

The detailed description may be set forth below with reference to the accompanying figures. In the figures, the left-most digit(s) of a reference number identifies the figure in which the reference number first appears. The use of the same reference numbers in different figures indicates similar or identical items. The systems and apparatuses depicted in the accompanying figures are not to scale and components within the figures may be depicted not to scale with each other.

DETAILED DESCRIPTION

Figure 1:
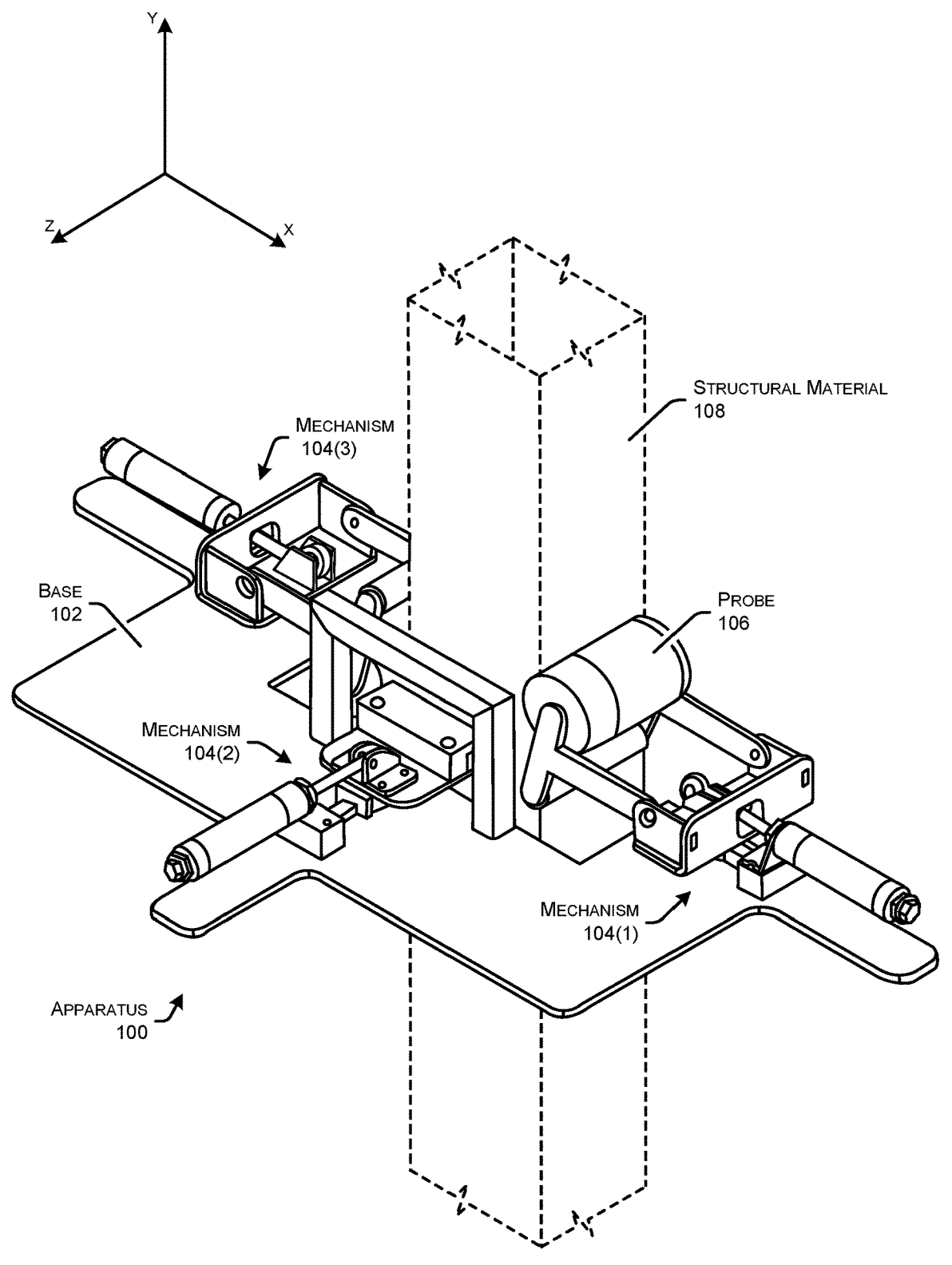
FIG. 1 is a top, front, right-side perspective view of an example apparatus according to the technologies disclosed herein, which may be used, among other things, for securing probes during an inspection, as illustrated.

As noted above, performing routine inspections on a hollow structural material (HSM) to check for deterioration can be extremely important. However, performing ultrasonic scanning on certain HSMs can be impractical and, therefore, entities may be required to expend a significant amount of resources to verify the integrity of such HSMs. Take, for example, a mine shaft that utilizes square tube steel as a primary support structure for an elevator that is used to lift several tons of material, equipment, and/or people at a time. In such a case, if one were to scan the square tube steel of the elevator to check the structural integrity of the steel, this would involve significant scanning to be done by hand for a single post/support. For instance, a technician would have to hold a probe (e.g., sensor, transducer, scanner, inspection tool, etc.) against each side of the square tube steel and at a specific pressure while the elevator was in motion. This would then have to be repeated for each side of the tube steel that is to be tested, as well as for each post/support of the elevator.

This disclosure is directed to an apparatus that, among other things, can be used to secure multiple probes and/or other inspection tools/devices for scanning structural materials (e.g., HSMs or other rigid materials). For example, the apparatus according to the techniques disclosed herein may be configured to secure one or multiple ultrasonic probes such that, when scanning a structural material, multiple ultrasonic scans can be captured in a single pass. For instance, if a section of square tube steel has three sides exposed, up to three probes may be coupled to the apparatus such that all three sides of the tube steel can be scanned in a single pass. However, in some examples, multiple probes may be disposed to scan each side of the tube steel (e.g., two, three, four, etc.) depending on the size and/or granularity of scan desired. In some examples, the apparatus may further be configured to couple to another rigid body for holding the apparatus in place for a scan. In continuing the mine shaft example from above, the apparatus may be configured to detachably couple to the mine shaft elevator or another rigid body that is capable of travelling up and down the mine shaft along the square tube steel.

Additionally, in some examples, the apparatus may be configured to press the coupled probes against the scanned surface (e.g., surface of the material being scanned) at a specific pressure (e.g., 10 PSI, 20 PSI, 30 PSI, 40 PSI, etc.) For instance, a probe may be detachably coupled to the apparatus via an air cylinder or other pressure adjustment mechanism. In this way, the pressure applied to a probe may be varied such that the probe is compressed against the scanned surface with more or less force. This may be done by increasing or decreasing an amount of air in the air cylinder. Additionally, the air cylinder may allow the probe(s) to move during a scan but still maintain pressure against the structural material. In some examples, movement of the probe while still maintaining pressure against a material being scanned is important as the material being scanned may not be uniform along its length. Although the examples described herein discuss the use of air cylinder(s), other adjustment mechanisms are contemplated. For instance, instead of an air cylinder, a spring, bolt, piston, hydraulic cylinder, pneumatic actuators, or the like may be used to maintain a desired amount of force applied on the probe.

In various examples, the apparatus described herein can be adjustable to fit different needs and applications. For instance, different types of probes, as well as different sizes of probes, may be coupled to the apparatus. Additionally, the apparatus may be adjusted to scan different sizes and/or shapes of structural material. Further, the apparatus can be adjusted to couple to different numbers of probes. For instance, the apparatus can be adjusted to couple to a first probe, a second probe, a third probe, and so forth. As used herein, the term "probe" may be used to refer to a sensor, scanner, or other inspection device/data gathering tool used for inspecting a structural material, composite inspection, corrosion mapping and monitoring, etc.

By way of example, and not limitation, an apparatus (e.g., device, system, etc.) according to the technologies disclosed herein for supporting one or more probe(s) during the performance of an ultrasonic or other non-destructive inspection (e.g., a phased array ultrasonic test) may include a base (e.g., a main body portion, a frame, etc.). In some examples, the base may be a plate or another form of rigid body. For instance, the base may be machined or cut from a metal plate (e.g., aluminum, steel, iron, titanium, etc.). In some examples, the base/metal plate may have a thickness in the range 0.1-0.8 inches. In some examples, the base may be solid or have a substantially homogenous thickness throughout. Additionally, or alternatively, the base may be skeletonized (e.g., to reduce weight), or hollow. In some examples, the base may be composed of any type of rigid material, such as metal, alloys, carbon fiber, plastic, wood, composites, or the like.

In some examples, the base may include a cavity. The cavity may include one or more sides, in some instances. In some examples, when a structural material is to be scanned, the apparatus may be positioned such that the structural material is inside the cavity. For example, if square tube steel is to be inspected, then the apparatus may be positioned such that a first side of the square tube steel is aligned with a first side of the cavity, a second side of the square stube steel is aligned with a second side of the cavity, and so forth. Details about the cavity of the base will be discussed in greater detail below with reference to the accompanying drawings.

In some examples, the apparatus may include a first mechanism for supporting a first probe. The first mechanism may be coupled or detachably coupled to the base. In some examples, the first mechanism may be positioned proximate a first side of the cavity. In some examples, the first mechanism may include first means for detachably coupling the first probe to the first mechanism. For instance, the first means may be a bracket, clamp, support arms, or other device that detachably couples the first probe with the first mechanism. In some examples, the first mechanism may include a pneumatic (air) cylinder, a hydraulic cylinder, a gas spring (strut), a mechanical spring assembly, or the like.

Additionally, in some examples, the first mechanism may be configured to, or otherwise capable of, apply(ing) an amount of force to the detachably coupled first probe. This amount of force may be a threshold amount of force associated with pressing the first probe against the material being inspected with sufficient pressure in order to obtain consistent and reliable measurement(s) from the first probe. For instance, the first mechanism may be configured to, or otherwise capable of, extend(ing) the first means in a first direction that may be substantially parallel to a plane defined by the base and into an area defined by the cavity. This extension capability may allow the first probe to be pressed against a first surface of the material being inspected for obtaining a first measurement.

For example, if the first mechanism is a pneumatic (air) cylinder, the pneumatic cylinder may be disposed proximate the first side of the cavity and substantially parallel to the plane defined by the base plate. Additionally, the pneumatic cylinder may include a body and a rod. In examples, the body may be coupled to the base plate proximate the first side of the cavity such that the rod can extend in the first direction that is into the area defined by the cavity. In such an example, as pressure inside of the pneumatic cylinder is increased, the rod may extend out of the body and further into the area defined by the cavity. In other words, as the pressure inside of the pneumatic cylinder is increased, the rod may extend out of the body and move the probe, which may be coupled to an end of the rod via the first means, closer toward the surface of the material being inspected. Additionally, as the air pressure is increased inside the cylinder, the amount of force applied to the probe may increase as well, and so may the pressure that the probe is applying to the surface. In some examples, the force and/or pressure may be proportional, or otherwise related to the amount of internal pressure that the pneumatic cylinder is filled to.

In some examples, the apparatus may further include a second mechanism for supporting a second probe. The second mechanism may be coupled or detachably coupled to the base. In some examples, the second mechanism may be positioned proximate a second side of the cavity. The second side of the cavity may be an opposite side to the first side of the cavity. Additionally, in some examples, the first side and the second side may be substantially parallel with one another. In some examples, the second mechanism may include second means for detachably coupling the second probe to the second mechanism. For instance, the second means may be a bracket, clamp, support arms, or other device that detachably couples the second probe with the second mechanism. In some examples, the second mechanism may include a pneumatic (air) cylinder, a hydraulic cylinder, a gas spring (strut), a mechanical spring assembly, or the like.

Additionally, in some examples, the second mechanism may be configured to, or otherwise capable of, apply(ing) the amount of force or a different amount of force (e.g., a second amount) to the detachably coupled second probe. This amount of force may be a threshold amount of force associated with pressing the second probe against the material being inspected with sufficient pressure in order to obtain consistent and reliable measurement(s) from the second probe. For instance, the second mechanism may be configured to, or otherwise capable of, extend(ing) the second means in a second direction, which may be (i) opposite to the first direction that the first mechanism extends, (ii) substantially parallel to the plane defined by the base, and/or (iii) into the area defined by the cavity. This extension capability may allow the second probe to be pressed against a second surface of the material being inspected for obtaining a second measurement simultaneously with the first measurement, described above.

For example, if the second mechanism is a pneumatic (air) cylinder, the pneumatic cylinder may be disposed proximate the second side of the cavity and substantially parallel to the plane defined by the base plate. Additionally, the pneumatic cylinder may include a body and a rod. In examples, the body may be coupled to the base plate proximate the second side of the cavity such that the rod can extend in the second direction that may be (i) opposite the first direction, (ii) substantially parallel to the plane, and/or (iii) into the area defined by the cavity. In such an example, as pressure inside of the pneumatic cylinder is increased, the rod may extend out of the body and further into the area defined by the cavity. In other words, as the pressure inside of the pneumatic cylinder is increased, the rod may extend out of the body and move the probe, which may be coupled to the end of the rod via the second means, closer toward the second surface of the material being inspected. Additionally, as the air pressure is increased inside the cylinder, the amount of force applied to the probe may increase as well, and so may the pressure that the probe is applying to the surface. In some examples, the force and/or pressure may be proportional, or otherwise related to the amount of internal pressure that the pneumatic cylinder is filled to.

In some examples, the apparatus may further include a third mechanism for supporting a third probe. The third mechanism may be coupled or detachably coupled to the base. In some examples, the third mechanism may be positioned proximate a third side of the cavity. The third side of the cavity may be between and/or perpendicular to the first side and the second side of the cavity. In some examples, the third mechanism may include third means for detachably coupling the third probe to the third mechanism. For instance, the third means may be a bracket, clamp, support arms, or other device that detachably couples the third probe with the third mechanism. In some instances, the third means may be different than the first means and/or the second means. In some examples, the third mechanism may include a pneumatic (air) cylinder, a hydraulic cylinder, a gas spring (strut), a mechanical spring assembly, or the like.

Additionally, in some examples, the third mechanism may be configured to, or otherwise capable of, apply(ing) the amount of force or a different amount of force (e.g., a third amount) to the detachably coupled third probe. This amount of force may be a threshold amount of force associated with pressing the third probe against the material being inspected with sufficient pressure in order to obtain consistent and reliable measurement(s) from the third probe. For instance, the third mechanism may be configured to, or otherwise capable of, extend(ing) the third means in a third direction, which may be (i) substantially perpendicular to the first direction and/or the second direction, (ii) substantially parallel to the plane defined by the base, and/or (iii) into the area defined by the cavity. This extension capability may allow the third probe to be pressed against a third surface of the material being inspected for obtaining a third measurement simultaneously with the first measurement and the second measurement, described above.

For example, if the third mechanism is a pneumatic (air) cylinder, the pneumatic cylinder may be disposed proximate the third side of the cavity and substantially parallel to the plane defined by the base plate. Additionally, the pneumatic cylinder may include a body and a rod. In examples, the body may be coupled to the base plate proximate the third side of the cavity such that the rod can extend in the third direction that may be (i) substantially perpendicular to the first direction and the second direction, (ii) substantially parallel to the plane, and/or (iii) into the area defined by the cavity. In such an example, as pressure inside of the pneumatic cylinder is increased, the rod may extend out of the body and further into the area defined by the cavity. In other words, as the pressure inside of the pneumatic cylinder is increased, the rod may extend out of the body and move the third probe, which may be coupled to the end of the rod via the third means, closer toward the third surface of the material being inspected. Additionally, as the air pressure is increased inside the cylinder, the amount of force applied to the probe may increase as well, and so may the pressure that the probe is applying to the third surface. In some examples, the force and/or pressure may be proportional, or otherwise related to the amount of internal pressure that the pneumatic cylinder is filled to.

In some examples, the base of the apparatus may include flange(s) or protrusion(s) disposed proximate the mechanism(s). In examples, the flange(s) or protrusion(s) may protect the mechanisms from being damaged, bumped, or the like. In some examples, the base may also include means for retaining a fluid applicator. The fluid applicator may be necessary, in some examples, for spraying the material and probes with water or other fluid to obtain a consistent and accurate measurement. In some examples, the apparatus may also include a handle. In some examples, the handle may be coupled to the base and disposed proximate a center of gravity of the apparatus.

In some examples, a method associated with using the apparatus and performing an ultrasonic inspection of a structural material may include techniques of positioning the structural material within the cavity associated with the apparatus. The techniques may also include configuring a first mechanism of the apparatus that is coupled to a first probe to apply an amount of force to the first probe, the amount of force associated with obtaining a first measurement from the first probe. The techniques may also include configuring a second mechanism of the apparatus that is coupled to a second probe to apply the amount of force to the second probe, the amount of force associated with obtaining a second measurement from the second probe. The techniques may also include causing a movement of the apparatus along a portion of the structural material in association with generating ultrasonic data during a data collection phase of the ultrasonic inspection.

The apparatus and techniques described herein can be implemented in a number of ways. For instance, in some examples, the mechanism(s) (e.g., the first mechanism, second mechanism, etc.) may be a rigid assembly for securing the probe(s). However, as will be apparent to users of the apparatuses described herein and those having ordinary skill in the art, a rigid assembly for securing the probe(s) may be less desirable as, in many cases, it is desirable for some movement to exist when a scan is being made (e.g., so that the probe(s) can move during a scan to account for changes in the physical structure of the material being scanned, which may be due to purposeful design, imperfections, load, repairs, or the like). In such a scenario with rigid support mechanisms, the base itself could be configured to have some movement or free play during a scan, and this may be acceptable in some situations. For instance, the base may include means for the whole apparatus to move with respect to a mounting point (e.g., mine elevator, cart, etc.), as opposed to the base being rigidly connected to the mounting point and the mechanism(s) being able to allow movement of the probe(s).

The apparatuses and techniques described herein can be implemented in a number of ways. Additional example implementations are provided below with reference to the following figures. Although discussed in example-specific contexts, the techniques and apparatuses described herein can be utilized in a variety of scenarios for securing inspection probes. For instance, the apparatuses described herein can be utilized to perform ultrasonic testing (or other types of testing) on structural materials in various settings or applications, such as bridges, buildings, energy production plants, material production plants, equipment, raw materials, or the like. In other words, the various aspects disclosed herein may be implemented in many different forms and should not be construed as limited to the implementations set forth herein. The disclosure encompasses variations of the embodiments, as described herein. In the following figures, like numbers refer to like elements throughout. Additionally, the reference axes included in the figures are the same orientation throughout.

FIG. 1 is a top, front, right-side perspective view of an example apparatus 100 according to the technologies disclosed herein, which may be used, among other things, for securing probes during an inspection, as illustrated. For instance, the apparatus 100 includes a base 102, and mechanisms 104(1)-104(3) (hereinafter referred to collectively as "mechanisms 104") for securing probes, such as the probe 106 secured by the first mechanism 104(1). The apparatus 100 may secure the mechanisms 104 during an inspection of a structural material 108, which may represent square tube steel, for instance.

With respect to the x, y, and z reference axes shown in FIG. 1, during an inspection, the apparatus 100 may be moved in a direction along the y axis to obtain measurements from the probes 106. Additionally, the first mechanism 104(1) may be configured to press the probe 106 against the surface of the structural material 108 with a specific amount of pressure during the inspection. Similarly, the second mechanism 104(2) and the third mechanism 104(3) may also press their coupled probe(s) against the surface of the structural material 108 with a specific amount of pressure, which may be dependent on the type of probe attached.

Figure 2:
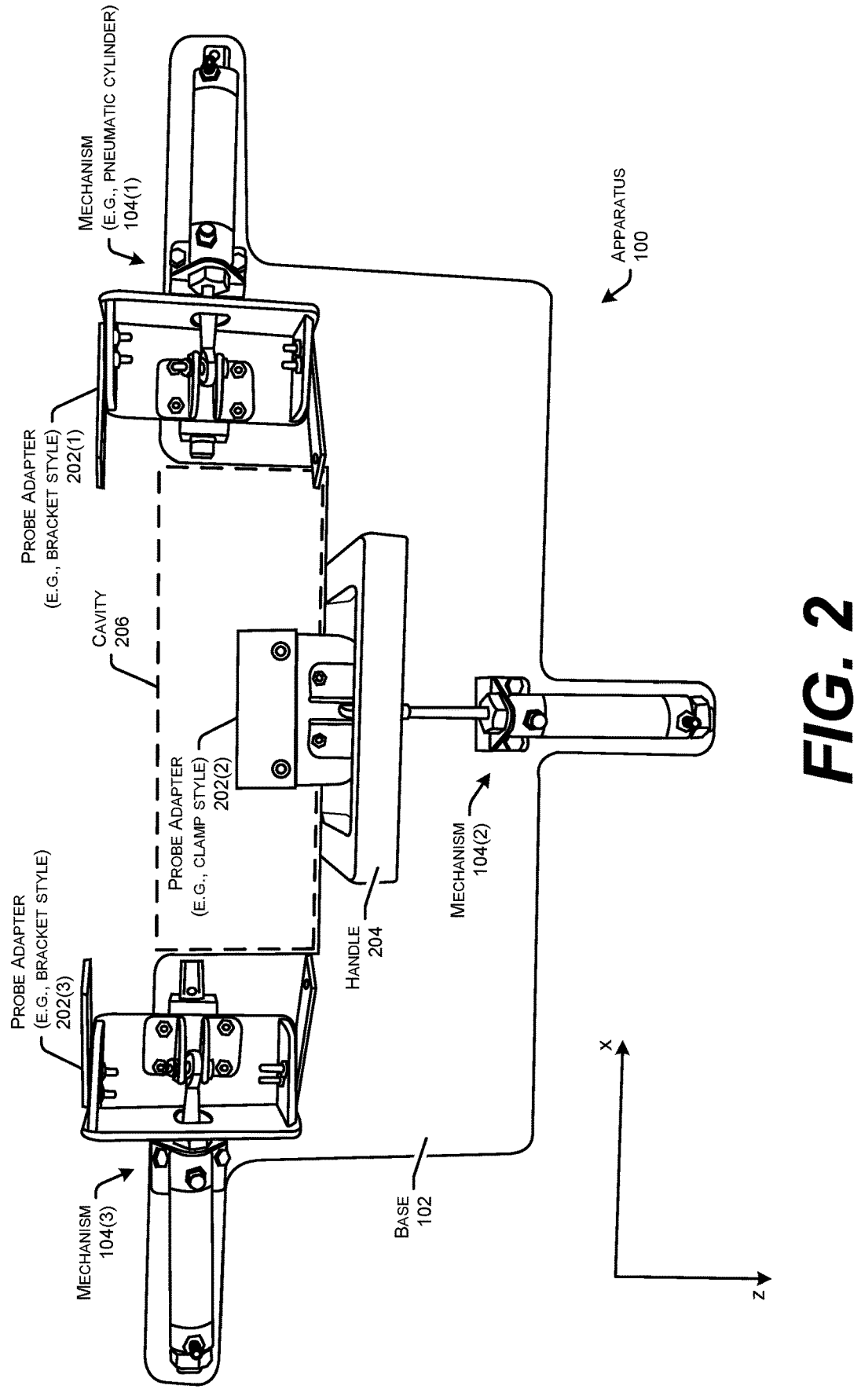
FIG. 2 is a top perspective view of the example apparatus.

FIG. 2 is a top perspective view of the example apparatus 100. From this view, additional detail is illustrated. For instance, the mechanisms 104 each include probe adapters 202(1)-202(3) (hereinafter referred to collectively as "probe adapters 202"). For instance, the first mechanism 104(1) includes a first probe adapter 202(1), the second mechanism 104(2) includes a second probe adapter 202(2), and the third mechanism 104(3) includes a third probe adapter 202(3). In the example shown in FIG. 2, the first probe adapter 202(1) and the third probe adapter 202(3) are a "bracket style" adapter, and the second probe adapter 202(2) is a "clamp style" adapter. In examples, the probe adapters 202 may allow different inspection probes to be coupled to the mechanisms 104. In some examples, the probe adapters 202 may be adjustable to accommodate different types and sizes of probes.

Additionally, the apparatus 100 includes a handle 204 that is coupled to the base 102. In some examples, the handle 204 may be utilized as a grab handle for handling the apparatus. Additionally, or alternatively, the handle 204 may be utilized as an accessory handle for attaching certain accessory devices to the apparatus 100. Such accessory devices may include, but not be limited to, fluid applicators, air applicators, electronic devices, lights, measuring equipment, additional probe(s), etc.

In some examples, the base 102 may be a plate or another form of rigid body. For instance, the base 102 may be machined or cut from a metal plate (e.g., aluminum, steel, iron, titanium, etc.). In some examples, the base 102 may have a substantially uniform thickness (e.g., in the range 0.1-0.8 inches). In some examples, the base 102 may be solid or have a substantially homogenous thickness throughout. Additionally, or alternatively, the base 102 may be skeletonized (e.g., to reduce weight), or hollow. In some examples, the base 102 may be composed of any type of rigid material, such as metal, alloys, carbon fiber, plastic, wood, composites, or the like.

In some examples, the base 102 may include a cavity 206. The cavity 206 may include one or more sides, in some instances. In some examples, when a structural material is to be scanned, the apparatus 100 may be positioned such that the structural material is inside the cavity 206. For example, if square tube steel is to be inspected, then the apparatus 100 may be positioned such that a first side of the square tube steel is aligned with a first side of the cavity 206, a second side of the square stube steel is aligned with a second side of the cavity 206, and so forth (e.g., as shown in FIG. 1).

The first mechanism 104(1) may be coupled or detachably coupled to the base 102. In some examples, the first mechanism 104(1) may be positioned proximate a first side of the cavity 206. In some examples, the first mechanism 104(1) may include first means for detachably coupling the first probe to the first mechanism 104(1). For instance, in FIG. 2, the first means include the probe adapter 202(1). In some examples, the first mechanism 104(1) may include a pneumatic (air) cylinder, as shown in FIG. 2, or a hydraulic cylinder, a gas spring (strut), a mechanical spring assembly, or the like.

Additionally, in some examples, the first mechanism 104(1) may be configured to, or otherwise capable of, extend(ing) the first means in a first direction (e.g., negative x direction) that may be substantially parallel to a plane defined by the base 102 and into an area defined by the cavity 206. This extension capability may allow the first probe to be pressed against a first surface of the material being inspected for obtaining a first measurement.

In some examples, the third mechanism 104(3) may be coupled or detachably coupled to the base 102. In some examples, the third mechanism 104(3) may be positioned proximate a second side of the cavity 206. The second side of the cavity 206 may be an opposite side to the first side of the cavity 206. Additionally, in some examples, the first side and the second side may be substantially parallel with one another. In some examples, the third mechanism 104(3) may include second means (e.g., probe adapter 202(3)) for detachably coupling the second probe to the third mechanism 104(3).

Additionally, in some examples, the third mechanism 104(3) may be configured to, or otherwise capable of, apply(ing) the amount of force or a different amount of force (e.g., a second amount) to the detachably coupled second probe. This amount of force may be a threshold amount of force associated with pressing the second probe against the material being inspected with sufficient pressure in order to obtain consistent and reliable measurement(s) from the second probe. For instance, the third mechanism 104(3) may be configured to, or otherwise capable of, extend(ing) the second means in a second direction (e.g., positive x direction), which may be (i) opposite to the first direction (e.g., negative x direction) that the first mechanism 104(1) extends, (ii) substantially parallel to the plane defined by the base 102, and/or (iii) into the area defined by the cavity 206. This extension capability may allow the second probe to be pressed against a second surface of the material being inspected for obtaining a second measurement simultaneously with the first measurement, described above.

In some examples, the second mechanism 104(2) may be coupled or detachably coupled to the base 102. In some examples, the second mechanism 104(2) may be positioned proximate a second side of the cavity 206. The third side of the cavity 206 may be between and/or perpendicular to the first side and the second side of the cavity 206. In some examples, the second mechanism 104(2) may include third means (e.g., probe adapter 202(2)) for detachably coupling the third probe to the second mechanism 104(2). In some instances, the third means may be different than the first means and/or the second means.

Additionally, in some examples, the second mechanism 104(2) may be configured to, or otherwise capable of, apply(ing) the amount of force or a different amount of force (e.g., a third amount) to the detachably coupled third probe. This amount of force may be a threshold amount of force associated with pressing the third probe against the material being inspected with sufficient pressure in order to obtain consistent and reliable measurement(s) from the third probe. For instance, the second mechanism 104(2) may be configured to, or otherwise capable of, extend(ing) the third means in a third direction (e.g., negative z direction), which may be (i) substantially perpendicular to the first direction and/or the second direction, (ii) substantially parallel to the plane defined by the base 102, and/or (iii) into the area defined by the cavity 206. This extension capability may allow the third probe to be pressed against a third surface of the material being inspected for obtaining a third measurement simultaneously with the first measurement and the second measurement, described above.

Figure 3:
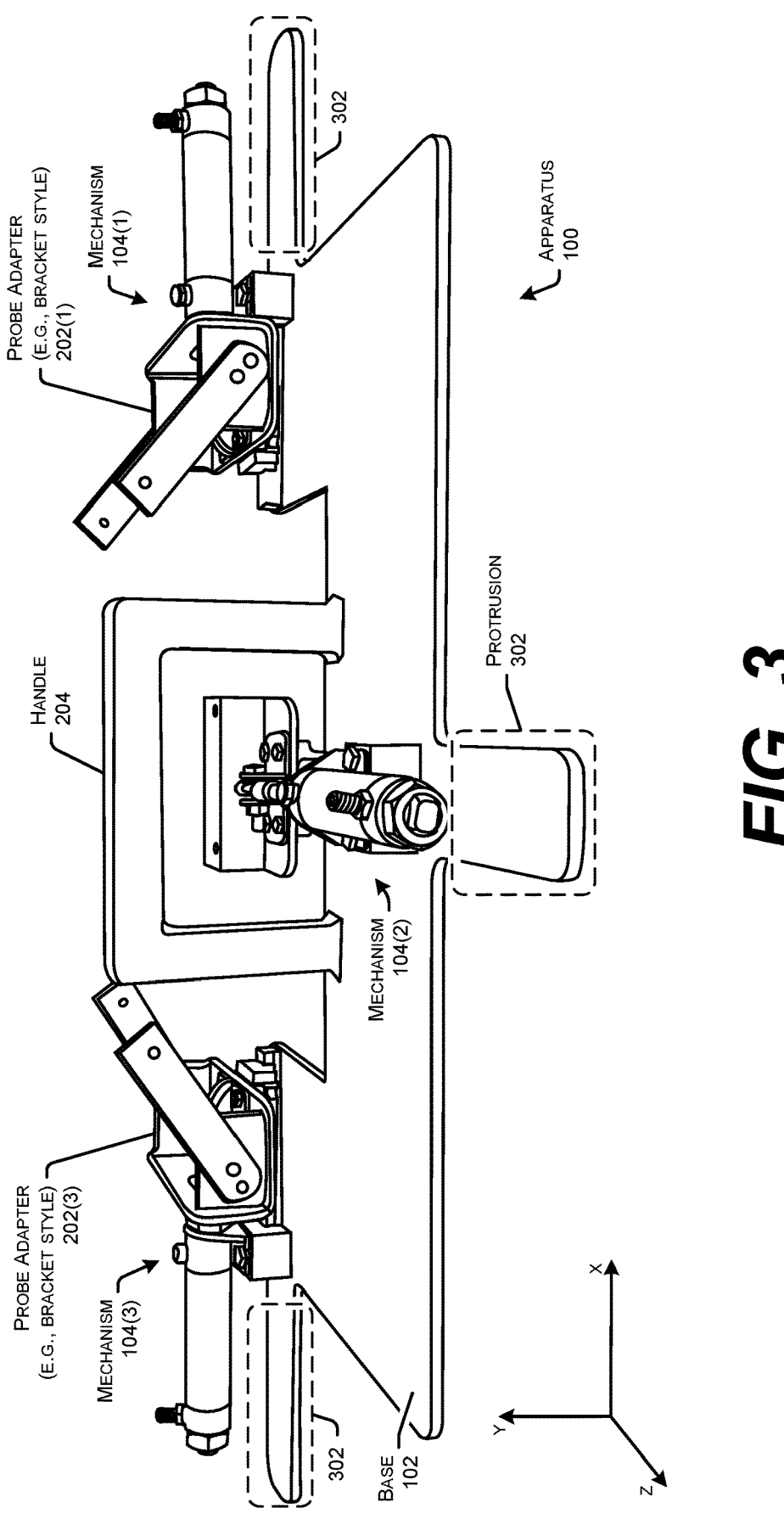
FIG. 3 is a top, front perspective view of the example apparatus.

FIG. 3 is a top, front perspective view of the example apparatus 100. From the view shown in FIG. 3, detail about the protrusions 302 of the base 102 are more apparent. For instance, the protrusions 302 protrude proximate the mechanisms 104, thereby protecting the mechanisms from being damaged or otherwise bumped, in some instances.

Figure 4:
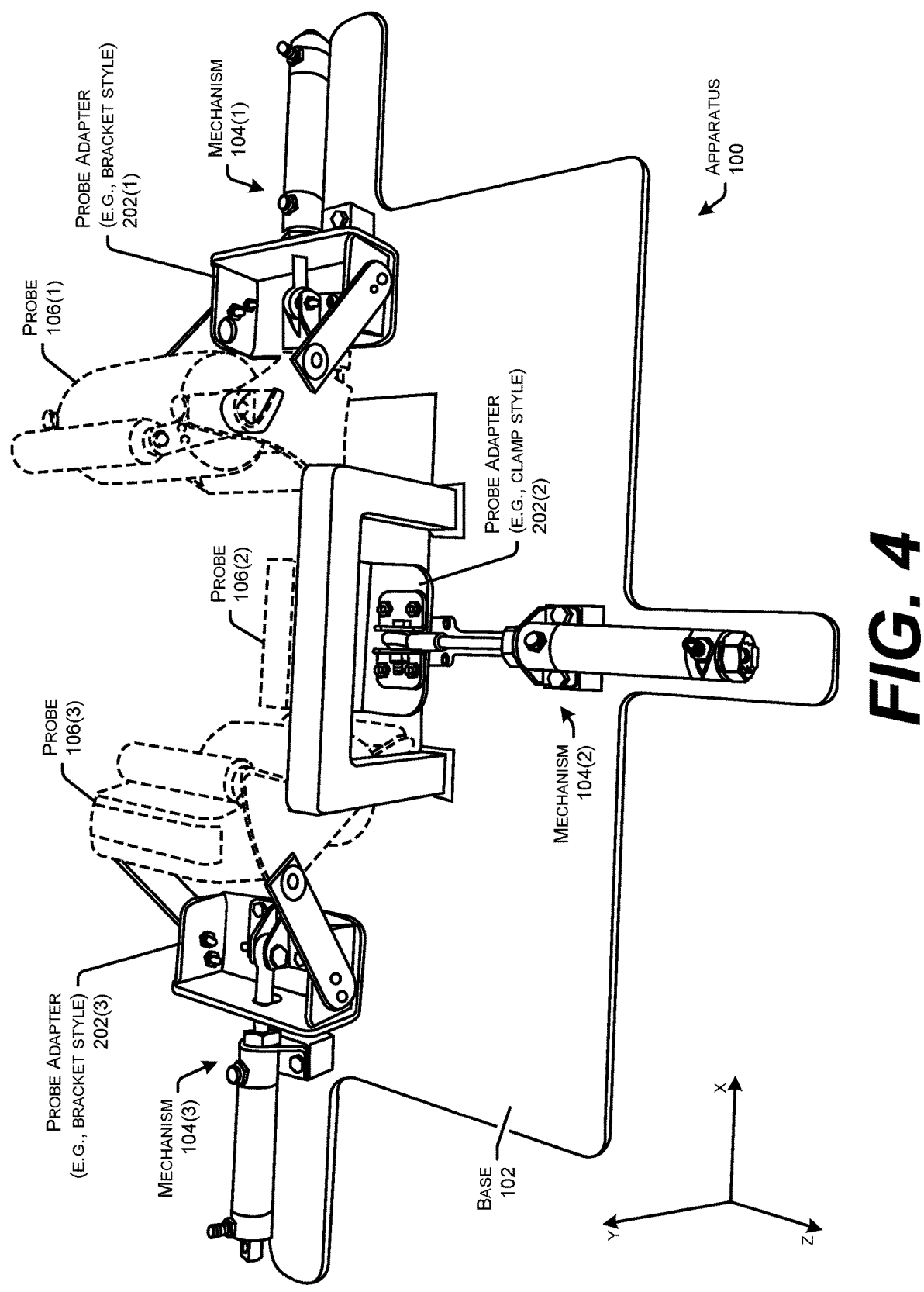
FIG. 4 is another top, front perspective view of the example apparatus, including some exemplary, detachably-coupled probes.

FIG. 4 is another top, front perspective view of the example apparatus 100, including some exemplary, detachably-coupled probes 106(1)-106(3). For instance, a first probe 106(1) (e.g., a wheel or roller type probe) is detachably-coupled to the first mechanism 104(1) via the first probe adapter 202(1). The second probe 106(2) is detachably-coupled to the second mechanism 104(2) via the second probe adapter 202(2). The third probe 106(3) is detachably-coupled to the third mechanism 104(3) via the third probe adapter 202(3).

Figure 5:
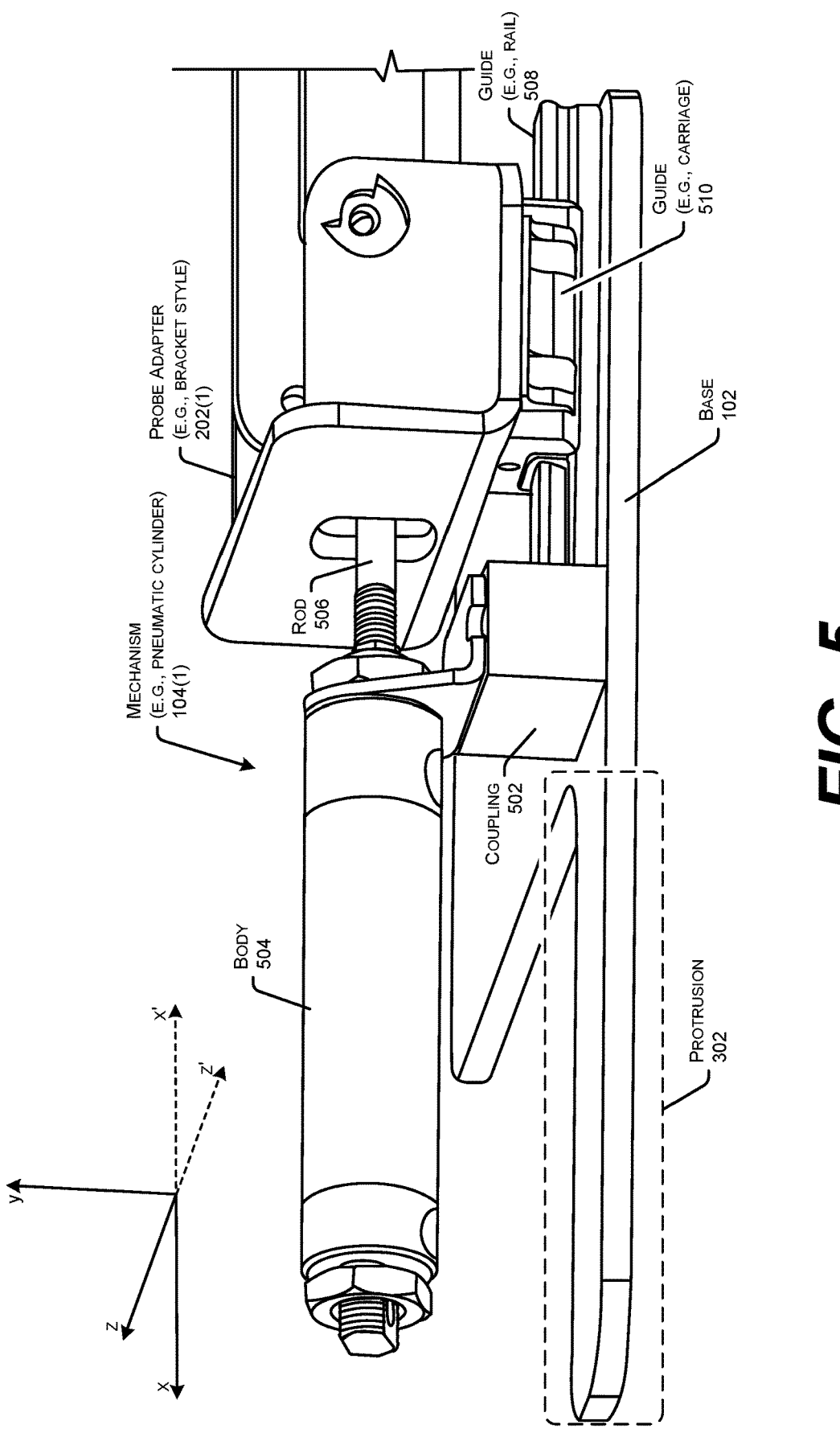
FIG. 5 is a top, back perspective view of an exemplary mechanism of the apparatus.
Figure 6:
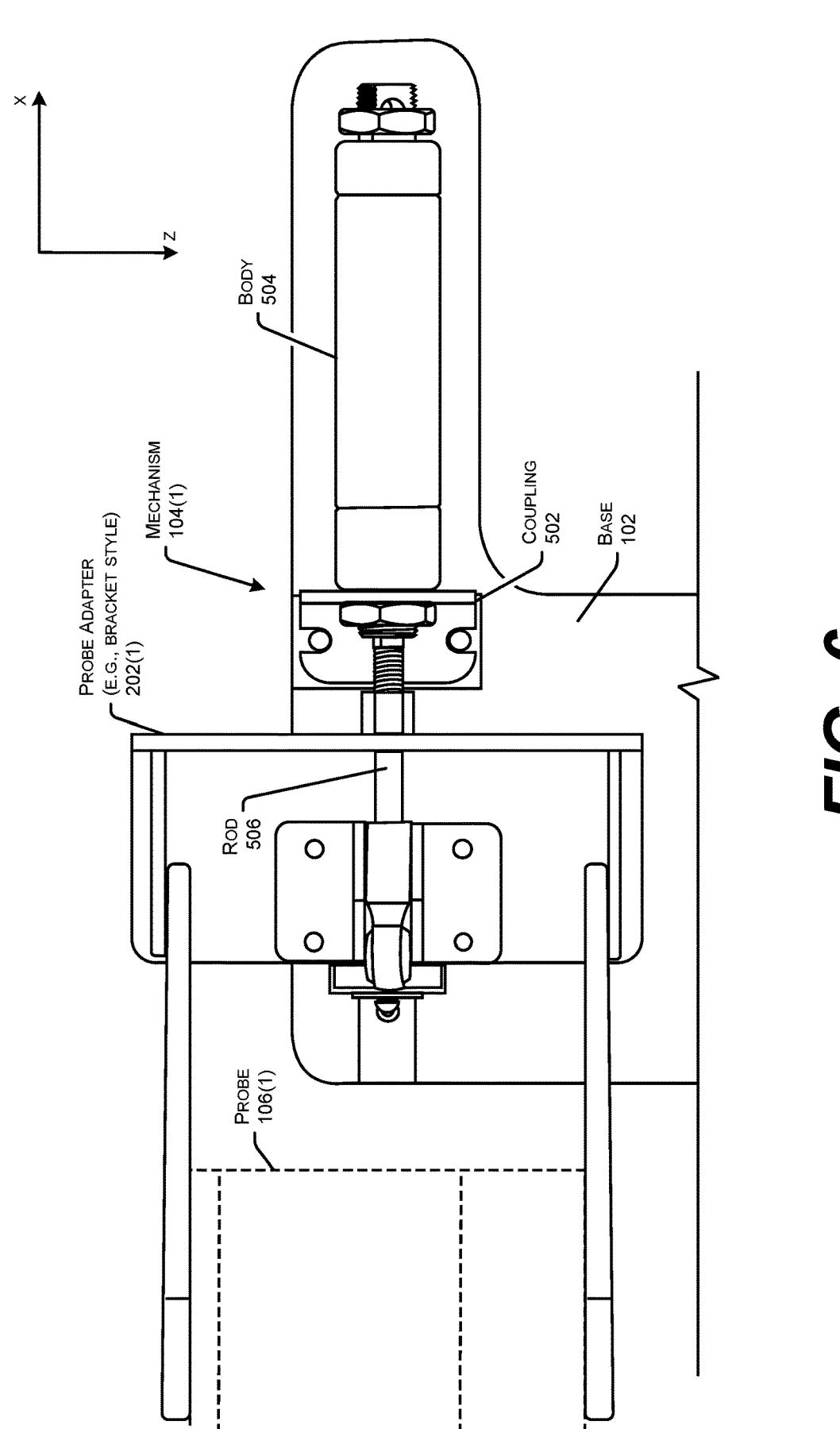
FIG. 6 is a top-down view of the exemplary mechanism and the exemplary, detachably-coupled probe.

FIG. 5 is a top, back perspective view of the exemplary mechanism 104(1) of the apparatus, and FIG. 6 is a top-down view of the exemplary mechanism 104(1) and the exemplary, detachably-coupled probe 106(1). The mechanism 104(1) shown in FIGS. 5 and 6 may be similar to or the same as the other mechanisms 104 described herein. For instance, the mechanism 104(1) may include a pneumatic cylinder that is coupled to the base 102 via a coupling 502. For instance, a body 504 portion of the pneumatic cylinder may be coupled to the body such that the body remains fixed relative to the base 102. In this way, a rod 506 of the pneumatic cylinder may be able to move relative to the base 102 to extend the probe adapter 202(1) coupled to the rod

506 into the cavity area, as described herein. In some examples, the mechanism 104(1) may also include one or more guides, such as the first guide 508 and the second guide 510. The first guide 508 shown in FIG. 5 is representative of a rail guide and the second guide 510 is representative of a carriage guide, which slides along the rail guide while the rail guide restricts the direction in which the carriage guide can travel. For instance, the first guide 508 (rail) allows the second guide 510 (carriage) to translate along the x axis. This ensures alignment of any detachably-coupled probe(s) during inspection, as well as helps secure the probe adapter to the base 102 while still allowing movement.

Figure 7:
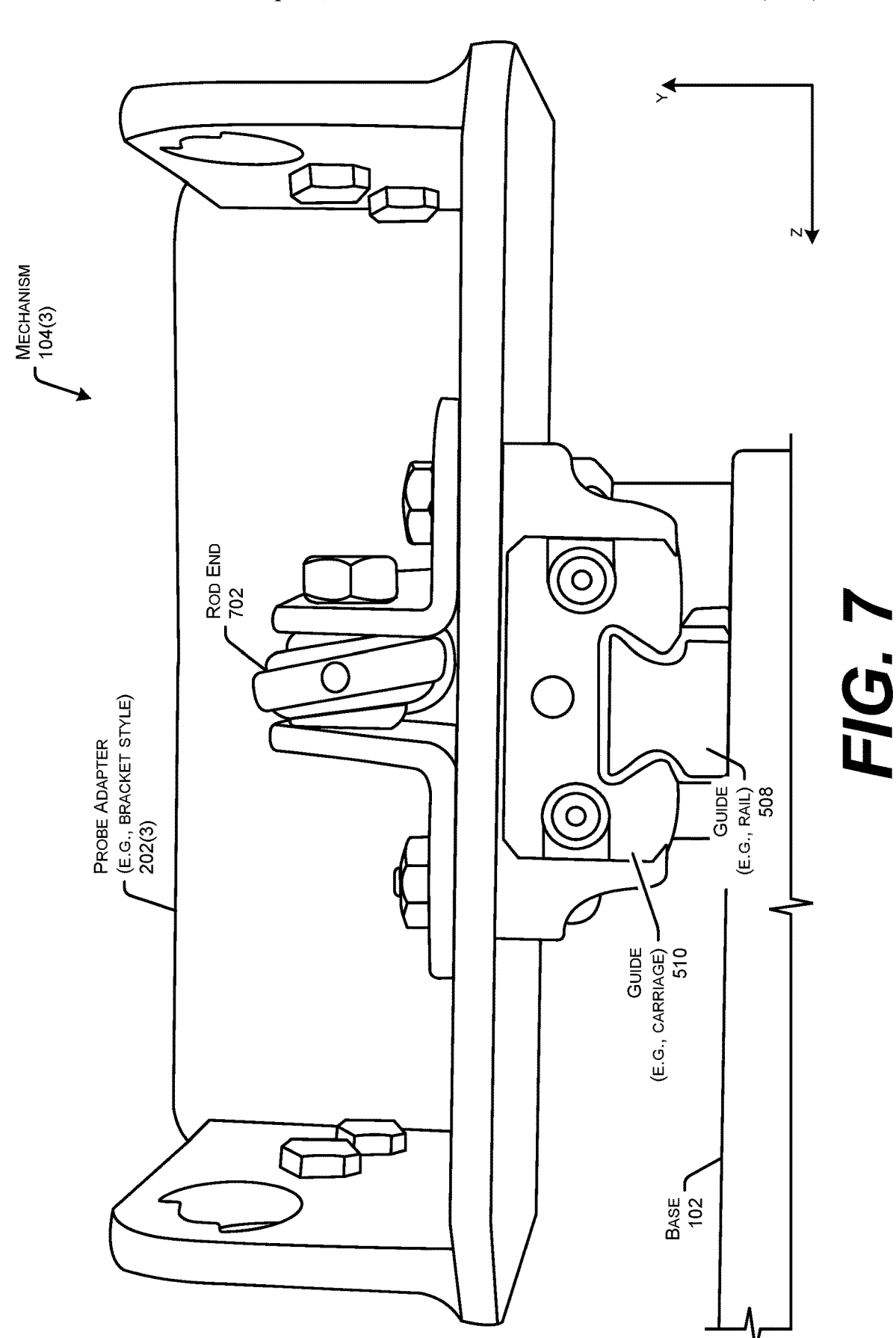
FIG. 7 is a right-side perspective view of the exemplary mechanism.

FIG. 7 is a right-side perspective view of the exemplary mechanism 104(3). Exemplary detail associated with the mechanism 104(3) can be seen in FIG. 7, including detail of the probe adapter 202(3), the first guide 508, the second guide 510, and the rod end 702.

Figure 8:
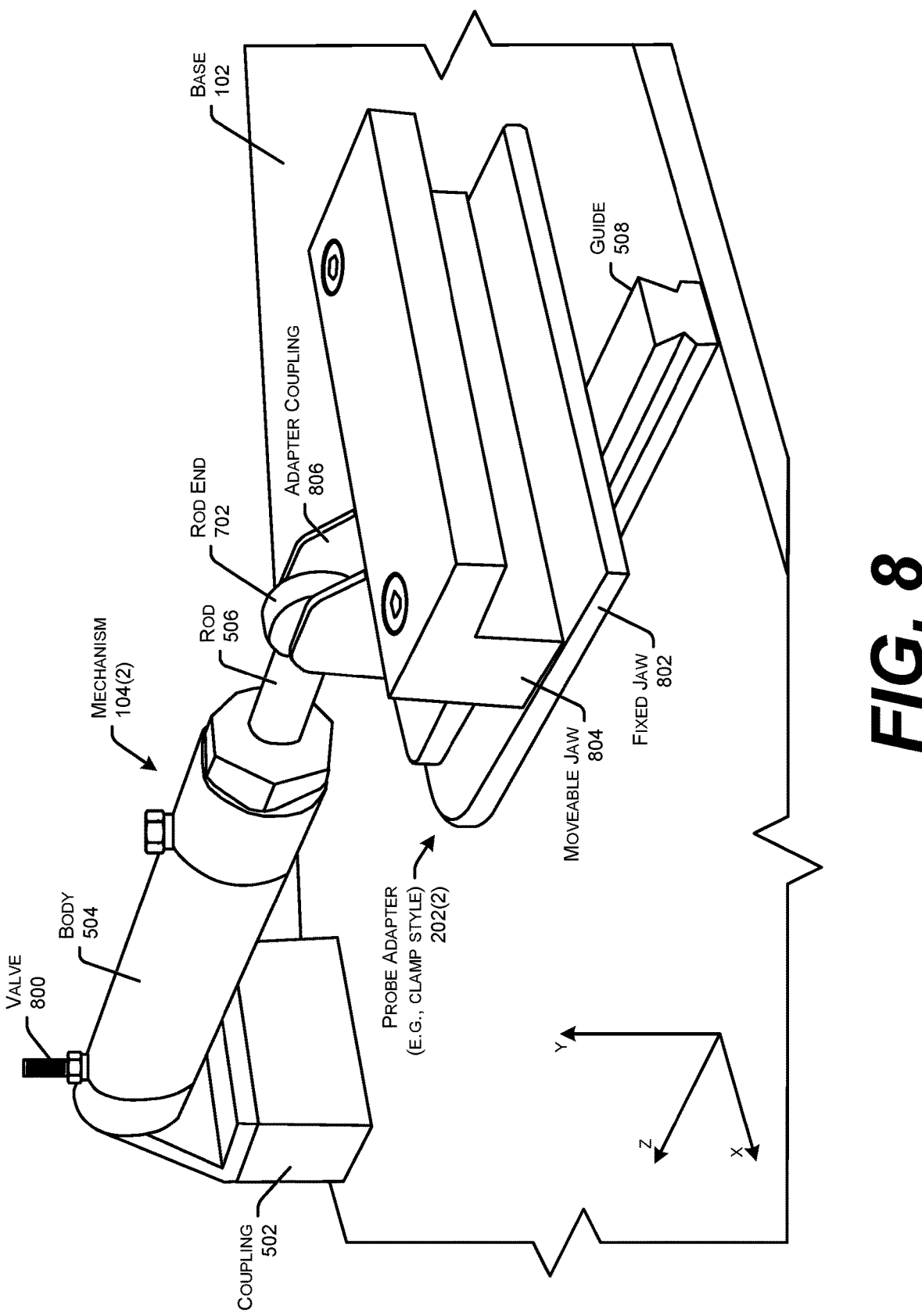
FIG. 8 is a top, back, right-side perspective view of another exemplary mechanism of the apparatus.

FIG. 8 is a top, back, right-side perspective view of another exemplary mechanism 104(2) of the apparatus. The mechanism 104(2) includes a pneumatic (air) cylinder. In examples, the body 504 of the pneumatic cylinder may be coupled to the base 102 via the coupling 502. The pneumatic cylinder may include a valve 800 for adjusting pressure within the cylinder and/or adjusting a distance the rod 506 protrudes from the body, an amount of force the rod 506 exerts on the probe adapter 202(2) and or coupled probe, an amount of force required to push the rod 506 into the body 504, etc. In examples, the rod 506 may extend in and out of the body 504 to translate the probe adapter 202(2) along the first guide 508 and in the direction of the z axis.

In examples, the probe adapter 202(2), which is a clamp style adapter, may include a fixed jaw 802, a moveable jaw 804, and an adapter coupling 806. In some examples, the fixed jaw 802 may be coupled to a carriage guide (similar to the second guide 510 described herein) that translates along the first guide 508 (e.g., the rail guide). Additionally, in some examples, the fixed jaw 802 and the moveable jaw 804 may be coupled together in a way that the two jaws can be adjusted to hold one or more probe(s). For instance, the moveable jaw 804 may move with respect to the fixed jaw 802 to clamp one or more probe(s) to the adapter. In examples, the adapter coupling 806 may be coupled to the fixed jaw 802 and to the rod end 702 of the rod 506.

Figure 9:
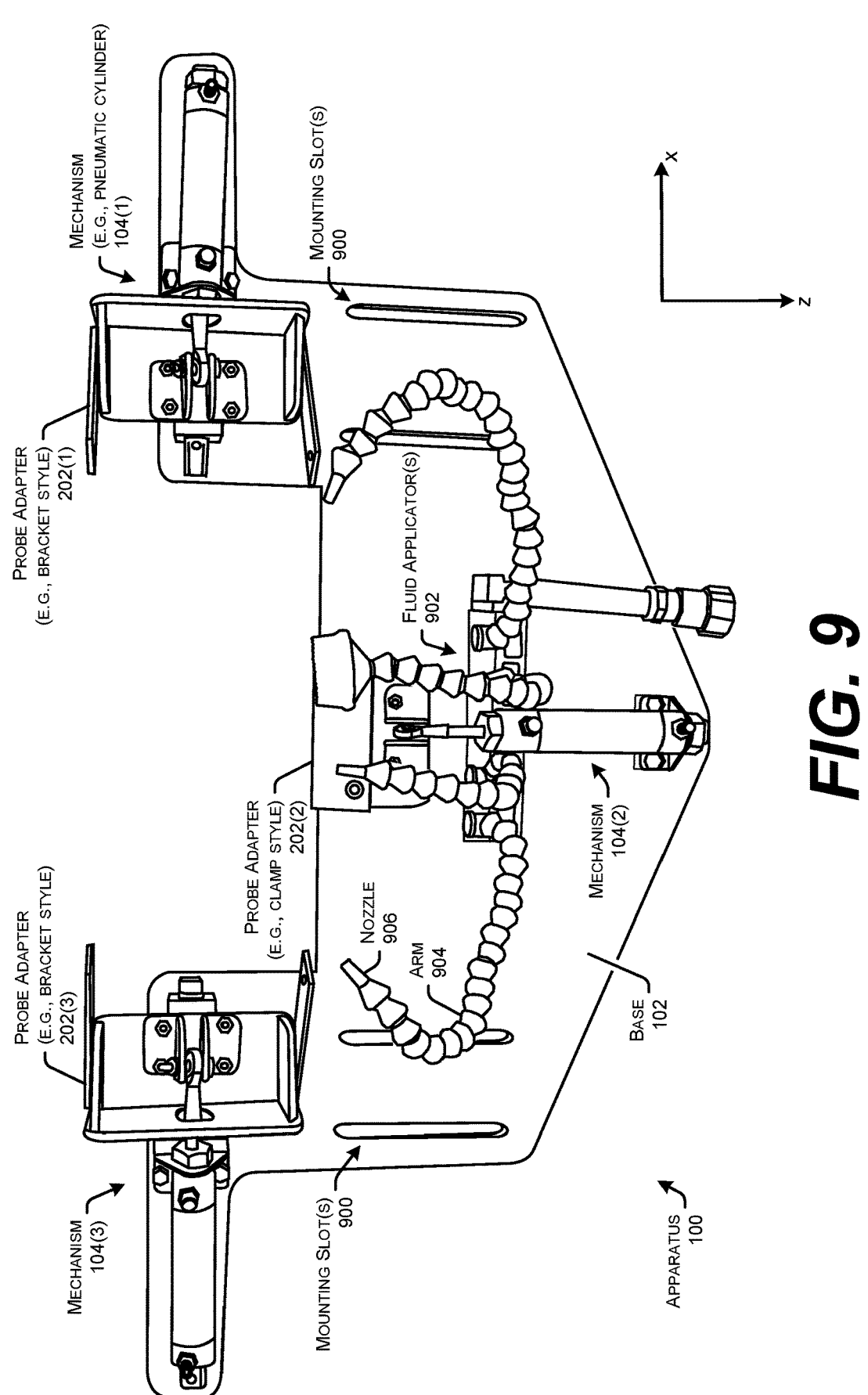
FIG. 9 is a top-down perspective view of another example apparatus according to the technologies disclosed herein.

FIG. 9 is a top-down perspective view of another example apparatus 100 according to the technologies disclosed herein. The apparatus 100 includes one or more mounting slot(s) 900 in the base 102, as well as one or more fluid applicator(s) 902. The fluid applicator(s) may include flexible arms 904 and spray nozzles 906. In some examples, the base 102 may include means for coupling the fluid applicator(s) 902 to the apparatus 100, such as structural tabs, adhesives, u-bolts, or the like. The fluid applicator(s) 902 may spray water or other fluids on the probes and/or structural material being scanned to help facilitate a consistent and accurate scan.

Figure 10:
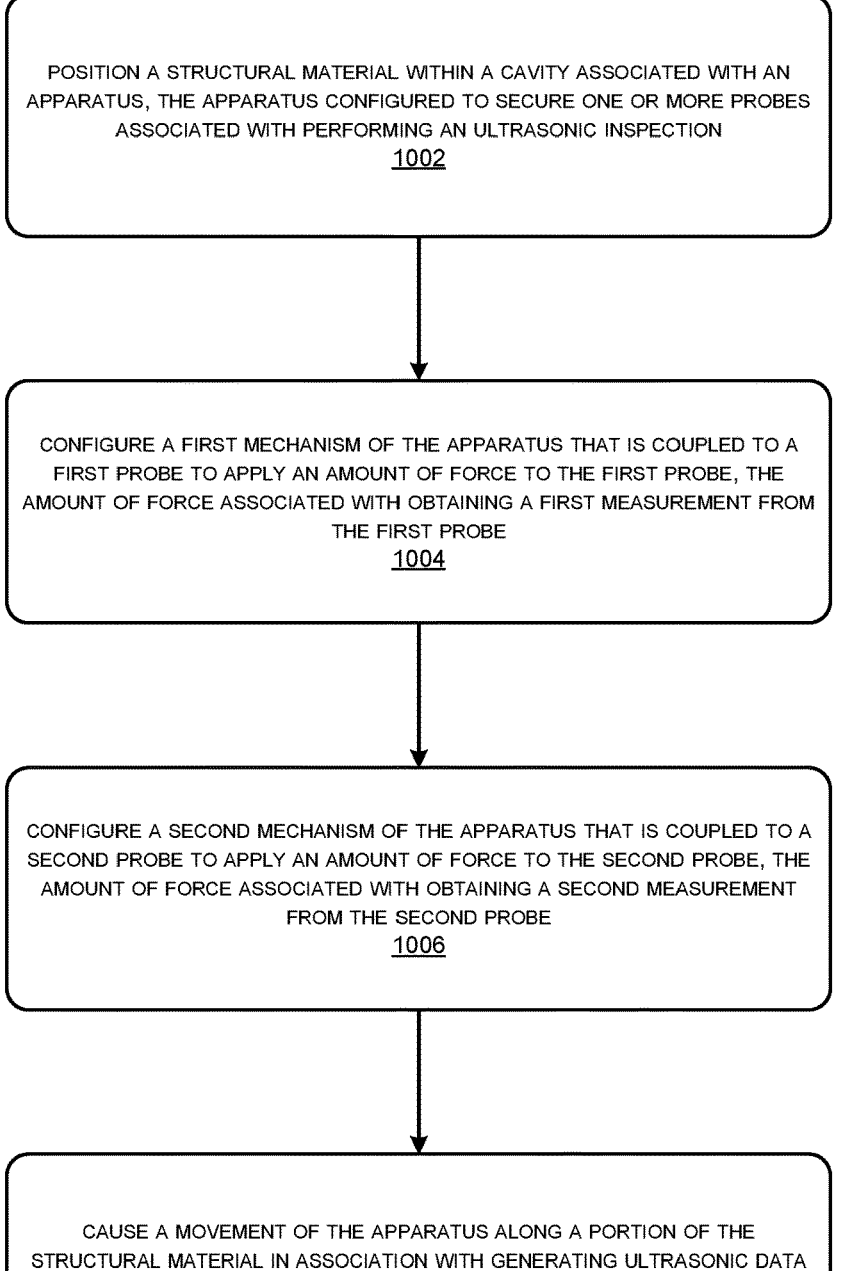
FIG. 10 is a flowchart illustrating an example method associated with utilizing an apparatus, as described herein, for securing probes during an inspection.

FIG. 10 is a flowchart illustrating an example method associated with utilizing an apparatus, as described herein, for securing probes during an inspection. The implementation of the various components described herein is a matter of choice. Accordingly, the logical operations described herein are referred to variously as operations or acts. It should also be appreciated that more or fewer operations might be performed than shown in FIG. 10 and described herein. These operations can also be performed in parallel, or in a different order than those described herein.

The method 1000 begins at operation 1002, which includes positioning a structural material within a cavity associated with an apparatus, the apparatus configured to secure one or more probes associated with performing an ultrasonic inspection. For instance, a user may position the structural material 108 within the cavity 206 associated with the apparatus 100.

At operation 1004, the method 1000 includes configuring a first mechanism of the apparatus that is coupled to a first probe to apply an amount of force to the first probe, the amount of force associated with obtaining a first measurement from the first probe. For instance, the user may configure the first mechanism 104(1) of the apparatus 100 that is coupled to the first probe 106(1) to apply the amount of force to the first probe 106(1).

At operation 1006, the method 1000 includes configuring a second mechanism of the apparatus that is coupled to a second probe to apply an amount of force to the second probe, the amount of force associated with obtaining a second measurement from the second probe. For instance, the user may configure the third mechanism 104(3) of the apparatus 100 that is coupled to the third probe 106(3) to apply the amount of force to the third probe 106(3).

At operation 1008, the method 1000 includes causing a movement of the apparatus along a portion of the structural material in association with generating ultrasonic data during the ultrasonic inspection. For instance, the user may cause the movement of the apparatus 100 along the portion of the structural material 108 in association with generating the ultrasonic data during the inspection.

While the foregoing invention is described with respect to the specific examples, it is to be understood that the scope of the invention is not limited to these specific examples. Since other modifications and changes varied to fit particular operating requirements and environments will be apparent to those skilled in the art, the invention may be not considered limited to the example chosen for purposes of disclosure, and covers all changes and modifications which do not constitute departures from the true spirit and scope of this invention.

Although the application describes embodiments having specific structural features and/or methodological acts, it may be to be understood that the claims are not necessarily limited to the specific features or acts described. Rather, the specific features and acts are merely illustrative some embodiments that fall within the scope of the claims of the application.

What is claimed is:

1. An apparatus comprising:
a base plate including a cavity disposed along an outer edge of the base plate, the cavity comprising a first side, a second side opposite the first side, a third side extending between the first and second sides, and an open side opposite the third side, the cavity configured to receive a structural material;
a first mechanism coupled to the base plate proximate the first side of the cavity, the first mechanism comprising a first actuator having a first rod and first means for detachably coupling a first probe to the first rod, the first mechanism configured to apply an amount of force associated with obtaining a first measurement using the first probe; and
a second mechanism coupled to the base plate proximate the second side of the cavity, the second mechanism comprising a second actuator having a second rod and second means for detachably coupling a second probe to the second rod, the second mechanism configured to apply the amount of force associated with obtaining a second measurement using the second probe; and a third mechanism coupled to the base plate proximate the third side of the cavity, the third mechanism comprising a third actuator having a third rod and third means for detachably coupling a third probe to the third rod, the third mechanism configured to apply the amount of force or a different amount of force associated with obtaining a third measurement using the third probe,
wherein the first rod, the second rod, and the third rod are each configured to extend into the cavity in different directions substantially parallel to a plane defined by the base plate to enable simultaneous inspection of multiple sides of the structural material.

2. The apparatus of claim 1, wherein the base plate further includes a first flange and a second flange, the first flange extending proximate the first mechanism and the second flange extending proximate the second mechanism.

3. The apparatus of claim 1, wherein the first actuator and the second actuator comprise at least one of:
pneumatic cylinders,
hydraulic cylinders,
gas springs, or
mechanical springs.

4. The apparatus of claim 1, further comprising third means for retaining a fluid applicator.

5. The apparatus of claim 1, wherein:
the first means comprises a first bracket for detachably coupling the first probe to the first mechanism, the first bracket configured to detachably couple to a first end of the first rod, and
the second means comprises a second bracket for detachably coupling the second probe to the second mechanism, the second bracket configured to detachably couple to a second end of the second rod.

6. The apparatus of claim 1, wherein the first rod, the second rod, and the third rod each extend through vertical planes that are perpendicular to the plane defined by the base plate and adjacent to the first side, the second side, and the third side of the cavity, respectively, and into the cavity.

7. The apparatus of claim 1, wherein each of the first mechanism, the second mechanism, and the third mechanism further comprise a guide assembly including a rail and a carriage configured to constrain movement of the corresponding rod along a linear path extending into the cavity.

8. The apparatus of claim 1, further comprising a valve in fluid communication with at least one of the first actuator, the second actuator, or the third actuator, the valve configured to regulate an internal pressure to adjust a force applied to the corresponding probe.

9. The apparatus of claim 5, wherein each of the first bracket and the second bracket comprise a quick-release coupling configured to enable tool-less detachment of a corresponding probe.

10. An apparatus for supporting multiple probes during performance of an ultrasonic test of a structural material, the apparatus comprising:
a base plate including:
a cavity that is configured to receive at least a portion of the structural material;
a first flange; and
a second flange;
a first pneumatic cylinder disposed proximate a first side of the cavity, the first flange, and substantially parallel to a plane defined by the base plate, the first pneumatic cylinder comprising:
a first body coupled to the base plate proximate the first side of the cavity, a first rod that extends in a first direction into an area defined by the cavity, and a first bracket that is configured to detachably couple a first ultrasonic probe to a distal end of the first rod, the first bracket further configured to position the first ultrasonic probe against a first surface of the structural material during the ultrasonic test; and a second pneumatic cylinder disposed proximate a second side of the cavity opposite the first side of the cavity, the second flange, and substantially parallel to the plane defined by the base plate, the second pneumatic cylinder comprising:

a second body coupled to the base plate proximate the second side of the cavity, a second rod that extends in a second direction opposite the first direction and into the area defined by the cavity, and a second bracket that is configured to detachably couple a second ultrasonic probe to a distal end of the second rod, the second bracket further configured to position the second ultrasonic probe against a second surface of the structural material opposite the first surface, wherein the first pneumatic cylinder and the second pneumatic cylinder are configured to simultaneously apply a controlled amount of force to the first ultrasonic probe and the second ultrasonic probe, respectively, to maintain acoustic contact with the structural material during the ultrasonic test.

11. The apparatus of claim 10, further comprising a third pneumatic cylinder disposed proximate a third side of the cavity between the first side and the second side and substantially parallel to the plane defined by the base plate, the third pneumatic cylinder comprising:

a third body coupled to the base plate proximate the third side of the cavity, a third rod that extends in a third direction that is substantially perpendicular to the first direction and the second direction and into the area defined by the cavity, and a third bracket that is configured to detachably couple a third ultrasonic probe to a distal end of the third rod, the third bracket further configured to position the third ultrasonic probe against a third surface of the structural material.

12. The apparatus of claim 10, further comprising third means for retaining a fluid applicator.

13. The apparatus of claim 10, wherein the first pneumatic cylinder and the second pneumatic cylinder are independently pressurizable to allow application of different forces to the respective ultrasonic probes during the ultrasonic test.

14. The apparatus of claim 10, further comprising a handle coupled to the base plate and positioned proximate a center of gravity of the apparatus to assist in manual positioning of the apparatus relative to the structural material.

15. The apparatus of claim 10, wherein the cavity is disposed along an outer edge of the base plate and comprises a first side, a second side opposite the first side, a third side extending between the first side and the second side, and an open side opposite the third side, such that the cavity defines a three-sided, open-ended region configured to receive the structural material, and wherein the first pneumatic cylinder, the second pneumatic cylinder, and a third pneumatic cylinder are disposed proximate the first side, the second side, and the third side of the cavity, respectively, to enable simultaneous inspection of multiple surfaces of the structural material.

16. A method associated with performing an ultrasonic test of a structural material using an apparatus that is configured to secure a plurality of ultrasonic probes during a data collection phase of the ultrasonic test, the method comprising:

positioning the structural material within a cavity disposed along an outer edge of a base plate of the apparatus, the cavity comprising a first side, a second side opposite the first side, a third side extending between the first and second sides, and an open side opposite the third side, such that the cavity defines a three-sided, open-ended region configured to receive the structural material;

configuring a first actuator of the apparatus that is coupled to a first ultrasonic probe to apply a controllable amount of force to the first probe, the amount of force associated with obtaining a first measurement from the first probe;

configuring a second actuator of the apparatus that is coupled to a second ultrasonic probe to apply the controllable amount of force to the second probe, the amount of force associated with obtaining a second measurement from the second probe; and simultaneously maintaining contact between the first probe and a first surface of the structural material and between the second probe and a second surface of the structural material opposite the first surface while causing a movement of the apparatus along a portion of the structural material, the movement associated with generating ultrasonic data during the data collection phase of the ultrasonic test.

17. The method of claim 16, wherein the first actuator is a first pneumatic cylinder and configuring the first actuator to apply the amount of force comprises pressurizing the first pneumatic cylinder such that a pressure within the first pneumatic cylinder meets or exceeds a threshold pressure.

18. The method of claim 16, wherein the first probe captures first ultrasonic data associated with a first side of the structural material and the second probe captures second ultrasonic data associated with a second side of the structural material opposite the first side.

19. The method of claim 16, wherein the first actuator and the second actuator comprise at least one of:

pneumatic cylinders, hydraulic cylinders, gas springs, or mechanical springs.

20. The method of claim 16, further comprising configuring a third actuator of the apparatus that is coupled to a third probe to apply the amount of force or a different amount of force to the third probe.

* * * * *